United States Patent [19]

Gould

[11] Patent Number: 4,882,927

[45] Date of Patent: Nov. 28, 1989

[54] METHOD AND APPARATUS FOR AUDITING MEANS USED FOR MEASURING CHARACTERISTICS OF A BULK MATERIAL

[76] Inventor: Gregory Gould, 30 Clairmont Ave., Thornwood, N.Y. 10594

[21] Appl. No.: 144,995

[22] Filed: Jan. 19, 1988

[51] Int. Cl.[4] .................... G01D 18/00; G01D 21/02; G01G 23/01

[52] U.S. Cl. ...................... 73/1 R; 73/1 B; 364/571.03

[58] Field of Search .................. 73/866, 1 R, 1 B, 73, 73/32 R, 433; 364/567, 571, 497, 498, 499, 571.01, 571.08; 177/50; 374/36; 422/68

[56] References Cited

U.S. PATENT DOCUMENTS

| | | | |
|---|---|---|---|
| Re. 29,132 | 2/1977 | List et al. | 177/59 X |
| 3,439,524 | 4/1969 | Rogers | 364/567 X |
| 3,687,802 | 8/1972 | Rummel et al. | 364/571 X |
| 3,807,860 | 4/1974 | Brainard, II | 364/571 X |
| 3,828,869 | 8/1974 | Sellers | 177/50 |
| 3,854,038 | 12/1974 | McKinley | 364/571 X |
| 3,976,150 | 8/1976 | Wilson et al. | 73/1 B X |
| 3,979,581 | 9/1976 | Reuland | 73/1 R X |
| 4,229,798 | 10/1980 | Rosie et al. | 364/571 X |
| 4,487,065 | 12/1984 | Carlin et al. | 364/571 X |
| 4,535,854 | 8/1985 | Gard et al. | 177/50 X |

FOREIGN PATENT DOCUMENTS

| | | | |
|---|---|---|---|
| 587341 | 1/1978 | U.S.S.R. | 177/50 |
| 767590 | 9/1980 | U.S.S.R. | 73/1 B |

*Primary Examiner*—Tom Noland
*Attorney, Agent, or Firm*—John L. Gray

[57] ABSTRACT

This invention concerns a method and an apparatus for auditing the devices used for measuring one or more characteristics of a bulk material, especially during handling or processing, and involves measuring one or more characteristics of the bulk material and concurrently measuring one or more variables which affect the accuracy or the reliability of the results obtained by the devices used to measure the particular characteristics of the bulk material.

112 Claims, 3 Drawing Sheets

METHOD AND APPARATUS FOR AUDITING MEANS USED FOR MEASURING CHARACTERISTICS OF A BULK MATERIAL

BACKGROUND OF THE INVENTION

Bulk materials such as bauxite, elemental sulphur, phosphates, gypsum, limestone, cement, iron ore, iron ore pellets, corn, wheat, and other grains, sugar, coal, lignite, peat, anthracite, waste products, sewage sludge, wood chips and bark, and paper regularly have various characteristics measured, especially during handling or processing. The value of these goods in the United States is enormous. For example, the forest products group, which is in Standard Industrial Class 26, had a total value of shipments in 1986 of about $108 billion. Of this amount pulp mills accounted for $4.1 billion, paper and board mills $42 billion, newspapers $23 billion, corrugated and solid fiber boxes $14 billion, sanitary paper products $11 billion, and sanitary food containers $3 billion. Coal is another bulk material which regularly has various of its characteristics measured, and in 1987 the forecast was for approximately $23 billion of coal to be mined and processed in the United States.

Among other bulk materials, nitrogenous and phosphatic fertilizers account for about $9 billion annually. Primary metals account for $50 to $60 billion and inorganic chemicals about $12 billion. In 1986 there was about $4 billion worth of cement produced in the United States.

Unfortunately in handling and processing some of these bulk materials significant errors arise, especially with respect to their weight, but errors also are found in other characteristics of the products.

As an example, coal is produced in the United States in about 5,000 mines operated by about 3,000 companies. Approximately 85 percent of total coal produced annually in the United States is consumed by the electric utility industry amounting to about $22.9 billion. Electric utility inventories are currently approximately 163 million tons with a nominal value of $5.5 billion.

The electric utility industry writes off up to five percent of inventories annually because of their inability to reconcile the quantities of coal purchased with the quantities burned. This corresponds to an annual write off of this product alone of $273 million. Since coal is essentially nonperishable in the ordinary time frames associated with the commerce of coal, such losses for the most part do not represent physical losses but rather inaccuracies in weighing. In general, weighing errors become increasingly positive with decreasing load. The errors that are experienced therefore tend to be exacerbated by and to the extent that materials handling operations are carried out at less than full capacity.

There are significant economic ramifications far beyond simple inventory corrections. For example, inaccuracies resulting in the overstatement of actual inventories must be compensated for by carrying an increment of extra inventory in order to be safe. The cost of purchase, stocking, interest, and insurance are very real though undefinable lacking more accurate figures. Additional economic ramifications are related to more accurate and timely quality information. The economic impact of forced derating of units and associated purchase of outside power, losses associated with less than ideal economic dispatch, and operation with coal quality better than actually needed to meet air quality regulations are examples. Again, such economic losses cannot easily be estimated lacking more accurate and timely information; however, they are substantial. The same problems arise in the other bulk materials industry which in dollar volume far exceeds that of coal.

There is a substantial need for sampling and weighing at bulk terminals through which bulk materials move, both in import and export markets. The United States produced about $4 billion worth of cement in 1986 and imported cement worth about $300 million. The value of metal and mineral mining shipments in Standard Industrial Classifications 10 and 14, which excludes fuels, was $23 billion in 1986. Imports amounted to $3.2 billion. The coal industry exported 88 million tons with the value estimated to be $3.5 billion.

SUMMARY OF THE INVENTION

This invention involves a method and apparatus of auditing and documenting operational variables or manifestations of such variables and the results obtained from the various pieces of equipment that are used for measuring one or more characteristics of a bulk material to authenticate that the accuracy and reliability of the results obtained from such measuring devices have not been impaired by variables which can influence the accuracy and reliability of said measuring devices. In doing this it is very useful concurrently to compare the measured characteristics with the measurements of variables which may affect the accuracy of the results obtained by the means used to measure the characteristics of the bulk materials with appropriate references.

It is therefore an object of this invention to provide a method and equipment to authenticate the accuracy and reliability of the results obtained from the measurement of various characteristics of bulk material.

It is a further object of this invention to provide such a method and apparatus which will enable both the measured characteristic and the results obtained from measuring the variables associated with the device that is used to measure the characteristics of the bulk material to be concurrently compared with one or more appropriate references.

The monitoring of operational variables and comparison with the appropriate references affords means for enhanced closed-loop control of operations within preselected limits beyond that afforded by bin level, plugged chute, and flow sensing controls, and for annunciating out of limit conditions which may require human intervention for correction or adjustment.

It is therefore an additional object of this invention to provide means for enhanced closed-loop control and annunciating out of limit operational conditions which may require human intervention for correction or adjustment.

These, together with other objects and advantages of the invention will become more readily apparent to those skilled in the art when the following general statements and descriptions are read in the light of the appended drawings.

DETAILED DESCRIPTION OF INVENTION

While this invention has been described with particular application of its use in the handling of coal in an electric utility, it should be kept in mind that it has equal application to other bulk materials as enumerated hereinabove.

It should also be understood that all of the components, except for the software for a particular installation, are off-the-shelf items that are readily available at the present time.

Figure 1:
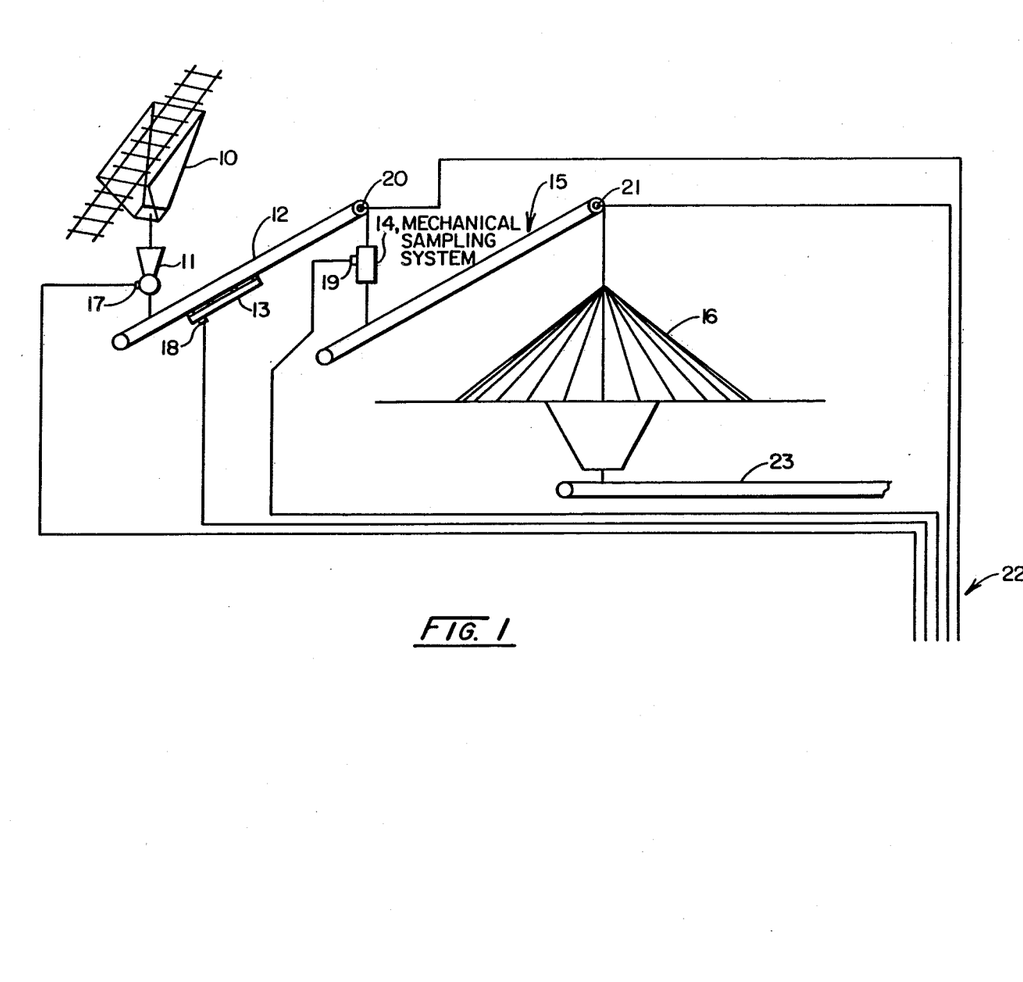
FIG. 1 is a schematic view of the invention as applied to the handling of coal from its receipt in a hopper car from the mine to removal from the storage pile to be sent to the burner.

Referring now to the drawings and particularly to FIG. 1, item 10 represents a rail siding track hopper unloading facility. Coal moves from the track hopper shown at 10 to a crusher 11 and thence to a belt 12 moving over a belt scale 13 and thus to a mechanical sampling system 14. From here the coal which is not removed in the mechanical sampling system 14 is carried upward on belt 15 and then discharged into storage pile 16. Track hopper 10 is typically equipped with a coarse screen referred to as a "grizzly" with openings about a foot square to prevent oversize lumps and large frozen masses of coal from becoming lodged in the system. Such lumps are broken down either manually or with special machines called "crackers". While the track hopper 10 is shown discharging directly into crusher 11 for simplification in explaining applicant's invention, in actual practice the coal flow from the tracker hopper 10 would be controlled by means of feeder conveyors.

Generally the facilities and equipment around an electric generating plant are designed to handle coal of nominally two inches top size. The main purpose of crusher 11 is to reduce the coal top size to meet this working requirement. The belt scale 13 represents a certified commercial scale. This means that the weights obtained from it are used for purposes of payment to the coal supplier. Sensors are located at 17 on crusher 11, 18 on belt scale 13, 19 on the mechanical sampling system 14, 20 on the belt 12, and 21 on belt scale 13. These sensors comprise one or more specific sensors as will be hereinafter described and are connected by means of input-output electrical channels 22–22 to the appropriate recording and monitoring devices shown in FIG. 4. The coal may be removed from the storage pile 16 as needed by means of conveyor 23.

Figure 2:
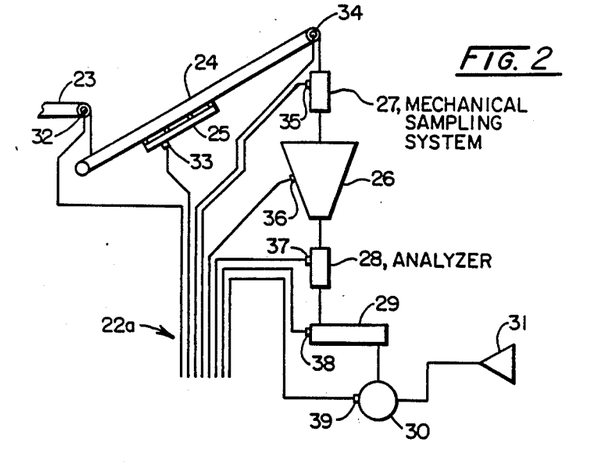
FIG. 2 is a schematic view of the invention as applied to the movement of coal through a mechanical sampling system, bunker, on-line analyzer, weight feeder, and pulverizer and thus to the burner.

Referring now more particularly to FIG. 2, the coal on conveyor 23 is transferred to conveyor 24 where again it passes over an additional belt scale 25. This belt scale 25 is generally a certificable scale but is not used as a commercial scale. Instead it is used to obtain the weight of coal that is burned. The coal drops from the end of conveyor 24 into bunker 26 with an appropriate amount being removed by means of mechanical sampling system 27 which is a typical mechanical sampling system usually identical to the mechanical sampling system 14. The coal may then move through an on-line analyzer 28, through a weigh feeder 29, and a pulverizer 30 to the burner 31. Again, sensors are located on belt 23 at 32, on belt scale 25 at 33, on belt scale 24 at 34, on mechanical sampling system 27 at 35, on bunker 26 at 36, on the on-line analyzer 28 at 37, on the weigh feeder 29 at 38, and on the pulverizer 30 at 39. These sensors comprise one or more specific sensors as will be hereinafter described and are connected by means of input-output electrical channels 22a–22a to the appropriate recording and monitoring devices shown in FIG. 4.

The commerce of coal is traditionally conducted on an "as received" (wet) basis analysis. This practice is the source of many disputes between buyer and seller. The moisture constituent is subject to loss by drainage and evaporation and gains from precipitation in the form of rain or snow. In northern climates frozen coal is a constant problem. Blockages frequently occur when wet, unfrozen coal comes in contact with metal surfaces that are below freezing temperature. Sensors at 17, 18, 19, 33, 35, 36, 37, and 38 are used to monitor and permanently record in real time with date and time stamps, ambient environmental temperature and metal temperatures for crusher 11, belt scale 13, mechanical sampling system 14, belt scale 25, mechanical sampling system 27, bunker 26, bunker 27, on-line analyzer 28, weigh feeder 29, as well as relative humidity for crusher 11 and mechanical sampling system 14. These data authenticate temperature and humidity conditions for reliable and accurate operation of sampling and weighing systems and permit setting alarms for conditions that are likely to cause operational problems or malfunctions of equipment.

Bulk commodities like coal occasionally are contaminated with adventitious materials that can be harmful to equipment. With coal, precautions are needed for everything from blasting caps to broken rail car parts. Magnetic separators are generally installed as early in a coal handling system as possible to protect the machinery from tramp iron. Despite precautions, such adventitious materials occasionally damage moving machinery. Sensors at 17, 18, 19, 33, 35, and 39 are used to monitor and permanently record in real time with date and time stamps, vibration and acoustic levels and patterns for crusher 11, belt scale 13, mechanical sampling system 14, belt scale 25, mechanical sampling system 27, and pulverizer 30 to authenticate operating conditions for reliable accurate operation of sampling and weighing systems. This additionally provides means for detecting excessive or unusual conditions that might impair sampling and weighing and also permits setting alarms for conditions that indicate operational problems and possible malfunctions of equipment. There is no clear boundary between audio frequencies and mechanical vibrations but generally mechanical vibrations associated with heavy machinery are below audio frequencies, so both are monitored and permanently recorded.

The product of impact crushers is affected dramatically by the tip speed of the hammers. Tip speed is a function of the speed of rotation. Load, voltage level, and power or current drawn by the crusher motor all affect speed of rotation. Also, motor temperature is affected by load and voltage. Both vibration and sound are affected by speed of rotation. Sensors at 17, 19, and 35 are used to monitor and permanently record in real time with date and time stamps the speed of rotation as well as the magnitude and frequency of vibrations and sounds that emanate from the crusher 11 and the crushers contained in mechanical sampling systems 14 and 27. The details of these sampling systems are described below with respect to FIG. 3.

In addition, one or more voltage, current, power, and motor temperature variables in real time with date and time stamps to authenticate operating conditions for reliable operation of these crushers is also recorded with sensors at 17, 19 and 35. This additionally provides means for detecting excessive or unusual conditions that might impair sampling and weighing and permits setting alarms for conditions that indicate operational problems and possible malfunctions of equipment. It also offers diagnostic opportunities for trouble shooting malfunctions as well.

Figure 3:
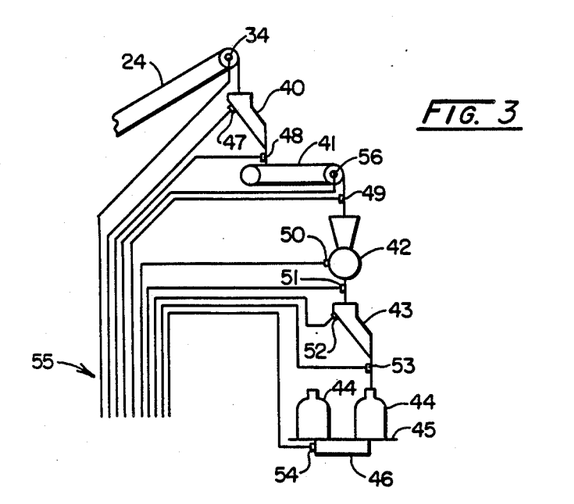
FIG. 3 is an enlarged schematic detail of the treatment of the coal in typical mechanical sampling systems shown in FIGS. 1 and 2.

Referring now more particularly to FIG. 3, there is depicted a detail of the samplers 14 and 17. Shown schematically is a typical two stage mechanical sampling system. This consists of a primary cutter 40, a primary feeder 41, a sample crusher 42, a secondary cutter 43, sample receivers 44—44, sample carousal 45, and sample scale 46. Appropriate chutes connect the various components and directs the coal through the sampling system. Three stage systems that include an additional stage of division by means of a tertiary cutter are not uncommon.

The handling properties of bulk materials vary with particle size distribution, moisture content and proportion of impurities. Coal is among the most intractable of all bulk materials. This situation is exacerbated by on-line crushing and division within the sampling system that alters the handling properties of the material and reduces mass flow rates in the divided sample to the point where friction, adhesion, and cohesion forces tend to override the inertial and gravitational forces that keep the coal in motion.

Blockages, hang-ups, irregular and discontinuous flows are potentially serious sources of error in the retained sample. Physical abuse of sampling systems often occurs when such conditions are encountered. Operating personnel are moved to hammer on the chute work, cutters and crushers with heavy pipes and sledge hammers to restore flow. Such abuse can permanently impair the performance of a sampling system.

Sensors located at 47, 48, 49, 50, 51, 52, 53, and 54 are used to monitor and permanently record in real time with date and time stamps the metal temperature, vibration and vibration patterns in connecting chutes, component enclosures and sample carousel 45 and sample scale 46 to document and authenticate operating conditions for reliable, accurate sampling. This surveillance permits setting alarms for conditions that indicate operational problems and possible malfunctioning of equipment or abuse and affords diagnostic opportunities for trouble shooting and malfunctions as well. These sensors comprise one or more specific sensors as will be hereinafter described and are connected by means of input-output electrical channels 55—55 to the appropriate recording and monitoring devices shown in FIG. 4.

There are two basic methodologies generally employed in the sampling of bulk materials, time basis and mass basis. For both types of sampling, national and international standards prescribe the minimum number and minimum mass of increments required relative to mass of the lot or consignment to be represented by the sample.

Time basis sampling extracts a sample increment at uniformly spaced time intervals. In order to maintain the same proportion of variable constituents in the sample as exists in the whole, the sample cutters which extract or divert the increment, must move at a fixed velocity the same for every increment.

Mass basis sampling extracts a sample increment at uniformly spaced mass intervals and the velocity of sample cutters must vary in direct proportion to variations in flow rate in order to maintain the same proportion of the variable constituents in the sample as in the whole.

With both time basis and mass basis sampling, serious error can accrue if cutter traverses occur in synchronization with linear variations in quality, relative to time or mass, or if secondary or tertiary cutter traverses occur in synchronization with preceding cutters in the system.

Linear variations in quality relative to time or mass are frequently related to variations in flow rate which in turn may reflect materials handling system capacity limitations associated with changing handling properties of the bulk material. Crushers also induce linear variations in quality relative to time or mass that is attributable to crushing of easier to crush material first.

Thus to authenticate operating conditions for accurate, reliable time and mass basis sampling, sensors located at 47, 52, and 56 are used to count the number of traverses of the primary cutter 40 and the secondary cutter 43 and to measure the speed of the primary feeder 41, and to measure and record in real time with date and time stamps the time at which traverses occurred, length of traverse cycle, the velocity of sample cutters for every traverse, and to determine whether cutters are operating in synchronization. This surveillance additionally permits setting alarms for conditions that indicate operational problems and possible malfunctioning of equipment and, of course, diagnostic opportunities for trouble shooting malfunctions as they occur.

Sensors located at 18 and 33 are used to monitor and permanently record in real time with date and time stamps the flow rate, voltage, and frequency of the power supply, ambient temperature, vibrations, and operating times of belt scales 13 and 25, and to authenticate the flow rates to sample systems 14 and 27 and to cross check synchronization of flow variations with cutter traverses.

Sensors located at 20, 21 in FIG. 1, 32 and 34 in FIG. 2, and 56 in FIG. 3 are used to monitor and permanently record in real time with date and time stamps conveyor speed, voltage, current (or power) to conveyor drive motors, or motors of hydraulic power packs for detecting fault conditions on conveyors 12, 15, 23, 24, and 41.

All conveyors of modern bulk materials handling systems are interlocked to prevent operation of any conveyor preceding another in the system which is not operating. For this reason, sensors to monitor the status of the existing controls is a viable alternative to the senors mentioned above recording information with respect to conveyor speed, voltage, etc.

In-transit dynamic weighing of materials in motion introduces numerous variables that can affect the accuracy of the weighments. Belt limberness and belt tension are among these. Temperature is a factor affecting the limberness of the belt. Temperature also affects analog and digital electronic devices. Many existing belt scales employ mechanical means for measuring belt travel (speed), and load, and integration of belt speed with load. Newer technologies employ electromechanical and electronic means for measuring belt speed, and load, and integration of belt speed with load. The accuracy of the latter is vulnerable to effects of radio frequency interference (RFI) and electromagnetic interference (EMI), as well as to voltage and frequency deviations in electrical power. Both mechanical and electronic scales are affected by deflections between adjacent idlers, and by vibrations that may be caused by such things as belt splices and nearby moving machinery, i.e., sampling systems and crushers.

The accuracy of belt scales is also affected by the load level. On commercial scales the load level is restricted by National Bureau of Standards Handbook 44 to a range of 35 percent to 100 percent of rated capacity. Alarms are required to signal operation outside these limits.

Sensors at 18 and 33 are used to monitor and permanently record in real time with date and time stamps the flow rate, voltage, and frequency of the power supply, ambient temperature, vibrations, and operating times of belts scales 13 and 25. This information with comparable information for the associated conveyors 12 and 24 is essential to authenticate the validity of weighments without adverse effect of such factors being measured.

Value has two dimensions, quantity (mass or number) and quality (valuable characteristics, properties or constituents). Society demands by means of laws and regulations that weighments for purposes of payment be made on certified scales.

Sampling of bulk materials is a complex demanding task for which the need for correctness, accuracy, and reliability has not achieved the same broad recognition of society in general as has weighing. As a result, no similar legal or regulatory certification requirements are placed on sampling. There are, however, national and international voluntary consensus sampling standards that are widely used in commerce by reference in contracts and agreements.

The advent of the on-line analyzer places bulk materials processes at the doorway of a new era in which the status of receipts, inventory and use can be maintained in real time in terms of valuable constituents and attributes as well as in more conventional units of mass such as tons or pounds. Typically, for example, electric utilities have resisted maintaining records of receipts, inventory and use of coal in terms of Btu heating value, the valuable property of the coal with which they are ultimately concerned, primarily because of the lack of timely heating value information. The advent of on-line analyzers capable of providing that information in real time, eliminates that issue. On-line analyzers which are available utilize x-ray fluorescence, microwave moisture analyzer, nuclear magnetic resonance, prompt gamma ray neutron activation analysis, and continuous calorimetry. Thus, the heating value of the combustible constituents in real time of coal is becoming obtainable.

Depending on where the on-line analyzer is situated in the bulk materials stream, sensor 37 located on the on-line analyzer 28 receives analytical data in real time related to the bulk materials being received, inventoried and used which is then entered into the data base maintained by the computer and associated software shown in FIG. 4 and described in greater detail hereinafter.

The factors that have been discussed herein are beyond those addressed by legislation and regulation which can impair the accuracy and reliability of certified scales. By measuring and permanently recording these factors in real time, the accuracy of weighments can be authenticated to a greater extent than heretofore was possible. By similar surveillance of machine sampling, conformance with applicable sampling standards, the correctness, accuracy and reliability of bulk materials samples can be raised to essentially the same level of authentication as certified weight. In combination with certified weights such sampling can effectively provide timely measurement of overall value with certified status.

Figure 4:
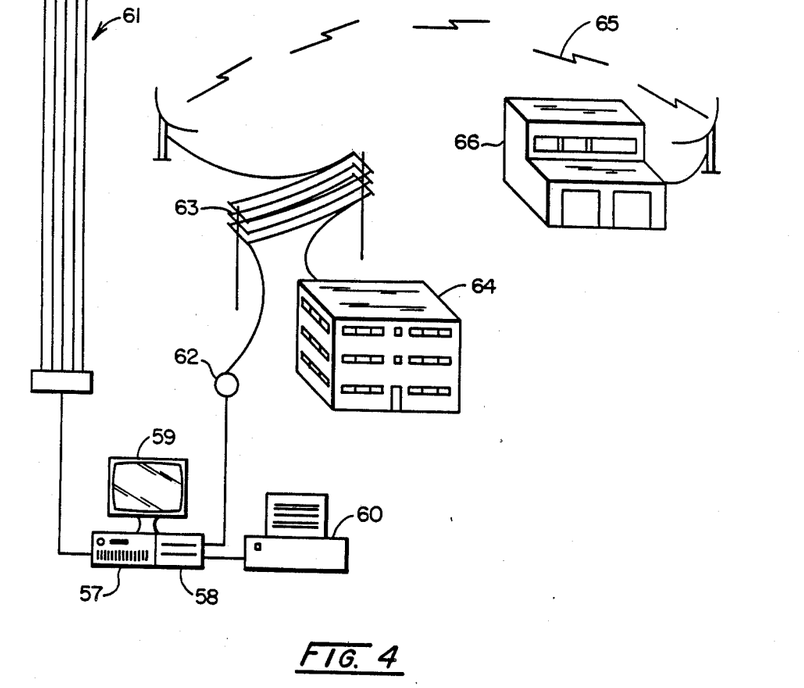
FIG. 4 schematically depicts computer software and peripherals employed in this invention for receiving, storing and analyzing data obtained from the various sensors utilized in the system which signal and record and maintain a data base of conditions of operations, malfunctions and failures, and reporting status of bulk materials, receipts, use and in inventory, locally and remotely, on video monitors and printed copy, and interfacing with main frame computers.

Referring now more particularly to FIG. 4, there is shown a computer 57 provided with disc drive system 58, video terminal 59, one or more printers 60, connected by input-output electrical channels 61 to the corresponding conduits shown in FIGS. 1-3 from the sensors. Also shown is modem 62, telephone link 63 to a main office 64, and a microwave link 65 to a central repair shop 66. Computer 57 is controlled by proprietary software that polls the various sensors in the system through multiple analog and digital input-output channels which condition the incoming signals. Computer 57 is equipped with an electronic clock calendar, disc drives for permanently recording data from the sensors, and necessary interfaces for modem, printer, and video terminal keyboard.

The software performs many services. It converts sensor signals into real world units, if necessary, directs the permanent recording of the sensor data in a database maintained on disc drive system 58, with date and time stamps from the internal electronic clock calendar, analyzes the sensor data for status relative to predesignated benchmarks, checks for sampling system operation in synchronization, and activates visual and audible alarms for any conditions outside predesignated limits, or requiring human attention or intervention.

In comparing the data obtained both from the device measuring the characteristics of the bulk material and the variables being measured concurrently with the measurement of the characteristics of the bulk materials, appropriate benchmarks can be selected as references. For example: Such benchmarks include contract, equipment, and process specifications, operating and material standards, purchase and acceptance specifications, regulatory and legal limits, and experience and empirically established limits.

The software also cross checks bulk material receipts with predesignated quality and quantity limits, and conversion of receipts, inventory and usage into real world mass, valuable constituents, valuable properties, and monetary terms. The software provides the necessary services for interactive keyboard input of biographical data, and maintains access security to various levels of the software and data by predesignated priority levels. The software generates interruption, failure, status, operations and diagnostic reports, locally and at remote terminals in the main office and repair shop. The software also provides for inputs and outputs to mainframe computers.

The implementation of this invention is site specific and must be customized to the particular needs of any given facility. It is desirable that the computer program instruction code be modular re-entrant code to facilitate this kind of customization. Such computer programs are readily prepared by qualified programmers familiar with structured assembly or higher level computer languages.

While this invention has been described in its preferred embodiment, it is to be appreciated that variations therefrom may be made without departing from the true scope and spirit of the invention.

What is claimed:

1. A method of auditing for accuracy or reliability of measurement a means used for measuring one or more characteristics of a bulk material which comprises the steps of measuring said one or more characteristics of said bulk material with said means, and concurrently measuring one or more variables, which variables are independent of said means for measuring said characteristics and which variables directly or indirectly affect the normal operation of said means and thereby affect the accuracy or the reliability of the results obtained by the means used to measure one or more characteristics of said bulk material.

2. The method of claim 1 wherein at least one of the measurements obtained by measuring said one or more variables which affects the accuracy of the results obtained by the means used to measure said bulk material characteristics is concurrently compared with an appropriate reference.

3. The method of claim 1 wherein the characteristics of said bulk material are measured during handling of said bulk material.

4. The method of claim 3 wherein the variable affecting the accuracy or the reliability of the measurement of the characteristic of said bulk material being measured is pressure within components involved in handling said bulk material.

5. The method of claim 3 wherein the variable affecting the accuracy or the reliability of the measurement of the characteristic of said bulk material being measured is electrical voltage supply to components involved in handling said bulk material.

6. The method of claim 3 wherein the variable affecting the accuracy or the reliability of the measurement of the characteristic of said bulk material being measured is the speed of rotation of components involved in handling said bulk material.

7. The method of claim 3 wherein the variable affecting the accuracy or the reliability of the measurement of the characteristic of said bulk material being measured is velocity of components involved in handling said bulk material.

8. The method of claim 3 wherein the variable affecting the accuracy or the reliability of the measurement of the characteristic of said bulk material being measured is velocity of said bulk material during the handling of said bulk material.

9. The method of claim 3 wherein the bulk density of said bulk material is measured as said bulk material moves through an analyzing device.

10. The method of claim 3 wherein the chemical composition of said bulk material is measured as said bulk material moves through an analyzing device.

11. The method of claim 3 wherein the moisture content of said bulk material is measured as said bulk material moves through an analyzing device.

12. The method of claim 3 wherein the variable affecting the accuracy or reliability of the measurement of the characteristic of said bulk material being measured is electrical frequency supply to components involved in handling said bulk material.

13. The method of claim 1 wherein manifestations of said variables are measured concurrently with the characteristics of said bulk material.

14. The method of claim 1 wherein the bulk materials are solid materials.

15. The method of claim 1 wherein the bulk materials are taken from the group consisting of rock, stone, clay, sand, minerals, amorphous solids and agricultural products.

16. The method of claim 15 wherein the bulk materials are taken from the group consisting of bauxite, elemental sulphur, phosphates, gypsum, limestone, cement, iron ore, iron ore pellets, corn, wheat and other grains, sugar, coal, lignite, peat, anthracite, waste products, sewage sludge, wood chips and bark, and paper.

17. The method of claim 1 wherein the characteristic of said bulk materials being measured is weight.

18. The method of claim 17 wherein the weight of said bulk material is measured as the bulk material moves over a weighing device.

19. The method of claim 1 wherein the characteristic of said bulk material being measured is its bulk density.

20. The method of claim 1 wherein the characteristic of said bulk material being measured is its chemical composition.

21. The method of claim 1 wherein the characteristic of said bulk material being measured is its moisture content.

22. The method of claim 1 wherein the characteristic of said bulk material being measured is an attribute of one or more of the constituents of said bulk material.

23. The method of claim 22 wherein the attribute of one or more of the constituents of said bulk material is measured as said bulk material moves through an analyzing device.

24. The method of claim 1 wherein the variable affecting the accuracy or the reliability of the measurement of the characteristic of said bulk material being measured is the level of the measured characteristic of said bulk material.

25. The method of claim 24 wherein the level of the characteristic of said bulk material is measured as said bulk material moves through an analyzing device.

26. The method of claim 1 wherein the variable affecting the accuracy or the reliability of the measurement of the characteristic of said bulk material being measured is ambient air movement.

27. The method of claim 1 wherein the variable affecting the accuracy or the reliability of the measurement of the characteristic of said bulk material being measured is temperature of the ambient air.

28. The method of claim 1 wherein the variable affecting the accuracy or the reliability of the measurement of the characteristic of said bulk material being measured is relative humidity.

29. The method of claim 1 wherein the variable affecting the accuracy or the reliability of the measurement of the characteristic of said bulk material being measured is mechanical vibration.

30. The method of claim 1 wherein the variable affecting the accuracy or the reliability of the measurement of the characteristic of said bulk material being measured is acoustical sound pattern.

31. The method of claim 1 wherein the variable affecting the accuracy or the reliability of the measurement of the characteristic of said bulk material being measured is flow rate of said bulk material.

32. The method of claim 1 wherein the variable affecting the accuracy or the reliability of the measurement of the characteristic of said bulk material being measured is interference from electromagnetic fields.

33. The method of claim 1 wherein the variable affecting the accuracy or the reliability of the measurement of the characteristic of said bulk material being measured is timing of operating cycles of the means used for measuring said characteristic.

34. The method of claim 1 wherein the variable affecting the accuracy or the reliability of the measurement of the characteristic of said bulk material being measured is the relative position of the means used to measure the characteristic of said bulk material to said bulk material.

35. The method of claim 1 wherein the variable affecting the accuracy or reliability of the measurement of the characteristic of said bulk material being measured is the position of said bulk material relative to the means used to measure the characteristic of said bulk material.

36. The method of claim 1 wherein date and time stamped permanent records are maintained of all measurements.

37. The method of claim 36 wherein the current status of all critical monitored variables and measurements are displayed on local and remote terminals.

38. The method of claim 37 wherein the relationships among variables and measurements are analyzed and evaluated by a microprocessor under software control.

39. The method of claim 1 wherein the variable affecting the accuracy or the reliability of the measurement of the characteristic of said bulk material being measured is the fluctuations in level of the measured characteristic of said bulk material.

40. The method of claim 1 wherein the variable affecting the accuracy or reliability of the measurement of the characteristic of said bulk material being measured is air movement internal to the means used to measure the characteristics of said bulk material.

41. The method of claim 1 wherein the variable affecting the accuracy or reliability of the measurement of the characteristics of said bulk material being measured is the fluctuations in temperature of the ambient air.

42. The method of claim 1 wherein the variable affecting the accuracy or reliability of the measurement of the characteristic of said bulk material being measured is the temperature of the surfaces of the means used to measure the characteristics of said bulk material.

43. The method of claim 1 wherein the variable affecting the accuracy or reliability of the measurement of the characteristic of said bulk material being measured is the temperature of the bulk material.

44. The method of claim 1 wherein the variable affecting the accuracy or reliability of the measurement of the characteristic of said bulk material being measured is dewpoint.

45. The method of claim 1 wherein the variable affecting the accuracy or reliability of the measurement of the characteristic of said bulk material being measured is the level of mechanical vibration.

46. The method of claim 1 wherein the variable affecting the accuracy or reliability of the measurement of the characteristic of said bulk material being measured is fluctuations in levels of mechanical vibration.

47. The method of claim 1 wherein the variable affecting the accuracy or reliability of the measurement of the characteristic of said bulk material being measured is sound level.

48. The method of claim 1 wherein the variable affecting the accuracy or reliability of the measurement of the characteristic of said bulk material being measured is changes in sound pattern.

49. The method of claim 1 wherein the variable affecting the accuracy or reliability of the measurement of the characteristic of said bulk material being measured is fluctuations in flow rate of said bulk material.

50. The method of claim 1 wherein the variable affecting the accuracy or reliability of the measurement of the characteristic of said bulk material being measured is fluctuations in pressure within components involved in handling said bulk material.

51. The method of claim 1 wherein the variable affecting the accuracy or reliability of the measurement of the characteristic of said bulk material being measured is electrical current supply to the components involved in handling or said bulk material.

52. The method of claim 1 wherein the variable affecting the accuracy or reliability of the measurement of the characteristic of said bulk material being measured is fluctuations in voltage supplied to components involved in handling said bulk material.

53. The method of claim 1 wherein the variable affecting the accuracy or reliability of the measurement of the characteristic of said bulk material being measured is the synchronization of operating cycles of the means used for measuring said characteristic.

54. The method of claim 1 wherein the variable affecting the accuracy or reliability of the measurement of the characteristic of said bulk material being measured is fluctuations in the speed of rotation of components involved in handling said bulk material.

55. The method of claim 1 wherein the variable affecting the accuracy or reliability of the measurement of the characteristic of said bulk material being measured is the fluctuation in velocity of components involved in handling said bulk material.

56. The method of claim 1 wherein the variable affecting the accuracy or reliability of the measurement of the characteristic of said bulk material being measured is the fluctuation in velocity of said bulk material during the handling of said bulk material.

57. The method of claim 1 wherein the variable affecting the accuracy or reliability of the measurement of the characteristic of said bulk material being measured is the alignment of the means used to measure the characteristic of said bulk material.

58. The method of claim 1 wherein the variable affecting the accuracy or reliability of the measurement of the characteristic of said bulk material being measured is fluctuations in current supplied to components involved in handling said bulk material.

59. Apparatus for auditing for accuracy or reliability of measurement a means used for measuring one or more characteristics of a bulk material which comprises a first means for measuring said one or more characteristics of said bulk material and a second means for concurrently measuring one or more variables which directly or indirectly affect the normal operation of said first means and which thereby affect the accuracy or the reliability of the results obtained by said first means, which variables are independent of said means for measuring said characteristics.

60. The apparatus of claim 59 which comprises a third means for comparing the measurements obtained by said second means with an appropriate reference.

61. The apparatus of claim 59 wherein said second means includes means for measuring manifestations of said variables.

62. The apparatus of claim 59 wherein said first means includes a scale.

63. The apparatus of claim 59 wherein said first means includes means for measuring bulk density.

64. The apparatus of claim 59 wherein said first means includes means for measuring the chemical composition of said bulk material.

65. The apparatus of claim 59 wherein said first means includes means for measuring the moisture content of said bulk material.

66. The apparatus of claim 59 wherein said first means includes means for measuring an attribute of one or more of the constituents of said bulk material.

67. The apparatus of claim 66 wherein said means for measuring an attribute of one or more of the constituents of said bulk material comprises means for measuring the heating value of combustible constituents of said bulk material.

68. The apparatus of claim 59 wherein said second means includes means for measuring the level of one or more of the characteristics of said bulk material measured by said first means.

69. The apparatus of claim 59 wherein said second means includes means for measuring amibient air movement.

70. The apparatus of claim 59 wherein said second means includes means for measuring air movement internal to said first means.

71. The apparatus of claim 59 wherein said second means includes means for measuring the temperature of ambient air.

72. The apparatus of claim 59 wherein said second means includes means for measuring fluctuations in temperature of the ambient air.

73. The apparatus of claim 59 wherein said second means includes means for measuring the surface temperature of said first means.

74. The apparatus of claim 59 wherein said second means includes means for measuring the temperature of said bulk material.

75. The apparatus of claim 59 wherein said second means includes means for measuring relative humidity.

76. The apparatus of claim 59 wherein said second means includes means for measuring dew point.

77. The apparatus of claim 59 wherein said second means includes means for measuring mechanical vibration.

78. The apparatus of claim 59 wherein said second means includes means for measuring levels of mechanical vibration.

79. The apparatus of claim 59 wherein said second means includes means for measuring the fluctuations in levels of mechanical vibration.

80. The apparatus of claim 59 wherein said second means includes means for measuring acoustical sound patterns.

81. The apparatus of claim 59 wherein said second means includes means for measuring sound levels.

82. The apparatus of claim 59 wherein said second means includes means for measuring changes in sound patterns.

83. The apparatus of claim 59 wherein said second means includes means for measuring changes in sound levels.

84. The apparatus of claim 59 wherein said second means includes means for measuring flow rate of said bulk material.

85. The apparatus of claim 59 wherein said second means includes means for measuring fluctuations in flow rate of said bulk material.

86. The apparatus of claim 59 wherein said second means includes means for measuring the pressure within components involved in handling said bulk material.

87. The apparatus of claim 59 wherein said second means includes means for measuring fluctuations in pressure within components involved in handling said bulk material.

88. The apparatus of claim 59 wherein said second means includes means for measuring electrical voltage supplied to components involved in handling said bulk material.

89. The apparatus of claim 59 wherein said second means includes means for measuring electrical current supplied to components involved in handling said bulk material.

90. The apparatus of claim 59 wherein said second means includes means for measuring the fluctuations in electrical voltage supplied to components involved in handling said bulk material.

91. The apparatus of claim 59 wherein said second means includes means for measuring fluctuations in electrical current supplied to components involved in handling said bulk material.

92. The apparatus of claim 59 wherein said second means includes means for measuring interference from external sources, said sources selected from the group consisting of electrical, radio frequency, x-ray, gamma ray, atomic and subatomic sources.

93. The apparatus of claim 59 wherein said second means includes means for measuring the timing of operating cycles of said first means.

94. The apparatus of claim 59 wherein said second means includes means for measuring the synchronization of operating cycles of said first means.

95. The apparatus of claim 59 wherein said second means includes means for measuring the speed of rotation of components involved in handling said bulk material.

96. The apparatus of claim 59 wherein said second means includes means for measuring fluctuations in the speed of rotation of components involved in handling said bulk material.

97. The apparatus of claim 59 wherein said second means includes means for measuring the velocity of components involved in handling said bulk material.

98. The apparatus of claim 59 wherein said second means includes means for measuring the fluctuation in velocity of components involved in handling said bulk material.

99. The apparatus of claim 59 wherein said second means includes means for measuring the velocity of said bulk material during the handling said bulk material.

100. The apparatus of claim 59 wherein said second means includes means for measuring fluctuations in velocity of said bulk material during the handling of said bulk material.

101. The apparatus of claim 59 wherein said second means includes means for measuring the relative position of said first means to said bulk material.

102. The apparatus of claim 59 wherein said second means includes means for measuring the alignment of said first means with respect to a reference orientation.

103. The apparatus of claim 59 wherein said second means includes means for measuring the position of said bulk material relative to said first means.

104. The apparatus of claim 59 wherein said first means includes means for measuring the moisture content of said bulk material.

105. The apparatus of claim 59 wherein said first means includes means for measuring an attribute of a constituent of said bulk material.

106. The apparatus of claim 59 wherein said first means includes means for measuring the variation in level of the characteristic of said bulk material being measured.

107. The apparatus of claim 59 which comprises a fourth means for preparing date and time stamped permanent records of all measurements made by said first and second means.

108. The apparatus of claim 59 which comprises a fifth means for displaying the current status of all critical monitored variables and measurements.

109. The apparatus of claim 59 which comprises a sixth means for analyzing and evaluating the relationships among monitored variables and measurements.

110. The apparatus of claim 109 wherein said means for analyzing and evaluating the relationships among monitored variables and measurements is a microprocessor under software control.

111. The apparatus of claim 59 wherein said first means includes means for measuring the fluctuation in moisture content of said bulk material.

112. The apparatus of claim 59 wherein said first means includes means for measuring the fluctuations in level of one or more of the characteristics of said bulk material measured by said first means.

* * * * *